United States Patent [19]

Van Moerkerken

[11] Patent Number: 5,616,617
[45] Date of Patent: Apr. 1, 1997

[54] FACE PIMPLES PREVENTION METHOD AND COMPOSITIONS

[76] Inventor: Arthur Van Moerkerken, 18761 W. Dixie Hwy., #209, North Miami Beach, Fla. 33180

[21] Appl. No.: 562,692

[22] Filed: Nov. 27, 1995

[51] Int. Cl.$^6$ .................... A01N 37/12; A61K 31/195
[52] U.S. Cl. .................... 514/561; 514/564; 424/9.2
[58] Field of Search .................... 514/561, 564; 424/9.2

[56] References Cited

U.S. PATENT DOCUMENTS

| | | | |
|---|---|---|---|
| 3,666,863 | 5/1972 | Swanbeck | 514/554 |
| 4,505,896 | 3/1985 | Bernstein | 514/356 |
| 4,839,159 | 6/1989 | Winter et al. | 514/556 |
| 5,420,106 | 5/1995 | Parab | 514/2 |
| 5,459,153 | 10/1995 | Leung | 514/561 |

OTHER PUBLICATIONS

CA85:159865, Sequin, 1976.
CA84:79595, Lubowe, 1970.
CA79:137505, Dussord et al, 1973.
Merck Manual 15th Edition, 1987, pp. 2277–2280.

*Primary Examiner*—Rebecca Cook
*Attorney, Agent, or Firm*—Otto S. Kauder

[57] ABSTRACT

Disclosed is the method of determining the effectiveness of an agent for the prevention of facial pimples or acne, comprising the steps of a) administering to a susceptible subject a quantity of a trigger substance reproducibly effective in producing within a period of four hours the appearance of at least two pimples on the face of the subject lasting for at least eight hours in the absence of treatment, b) administering to said subject having received said quantity of trigger substance a predetermined quantity of the agent whose effectiveness is to be determined, c) measuring the number of pimples on the face of the subject upon administering said agent, and d) comparing the number of pimples with and without the administration of said agent.

Also disclosed are effective quantities of certain nutrient substances which can reproducibly relieve pimples produced in a susceptible subject by the administration of a trigger substance.

6 Claims, No Drawings

FACE PIMPLES PREVENTION METHOD AND COMPOSITIONS

This invention relates to the prevention of facial pimples, also known as acne. More particularly, this invention relates to the avoidance or at least mitigation of a tendency in some individuals to develop the symptoms of superficial acne, characterized by comedones, either open (blackheads) or closed (whiteheads), inflamed papules, superficial cysts, and papules; as well as deep acne, deep inflamed nodules and pus-filled cysts, which often rupture and become abscesses (see Merck Manual, 16th edition, 1992, pages 2430–2431). As stated in this reference work "Acne is often exacerbated in winter and improved in summer, probably because of the sun's beneficial effect. Diet has little effect, if any; however, if a food is suspected, it should be omitted for several weeks and then eaten in substantial quantities to see if eating it makes any difference. Most such trials prove that the acne is unrelated to food. Acne may cycle with the menses, and it may clear or become worse during pregnancy. In many women who first develop acne in their 20s and 30s certain cosmetics may act as aggravating agents."

Thus the sufferer is told that the problem may have any of a number of possible causes, and the probability of success in controlled experimentation attempting to correlate the problem with a particular food is small.

While the disease is stated to be almost universal and the prognosis for eventual healing without scars is considered good, disfiguring or even mild acne may embarass young people and lead to psychological complications, so that supportive counseling for both patients and their parents is often recommended. Specific treatments for superficial acne include cautious mechanical removal of comedones, topical clindamycin solution or other antibiotics, or 5–10% preparations of benzoyl peroxide, considered the best nonprescription topical drug (Merck Manual).

For deep acne, topical treatment is stated in this reference to be unsatisfactory. Treatment of patients with a few deep lesions is usually a broad-spectrum oral antibiotic; the most effective antibiotic with the fewest side effects is said to be tetracycline in doses of 250 mg four times a day or 500 mg twice a day, except that for pregnant patients similar doses of erythromycin are said to be preferred. Treatment should be continued for four weeks and then decreased to "the lowest amount that gives a good response." However, because relapse ordinarily follows short periods of treatment, therapy must be continued for months to years with "as little as 250 or 500 mg per day of tetracycline often sufficient."

Oral isotretinoin is considered the best treatment for patients in whom treatment with antibiotics is unsuccessful or with very severe deep acne but is subject to severe side effects and cannot be given to pregnant women because it is teratogenic.

L. H. Leung U.S. Pat. No. 5,459,153 of Oct. 17, 1995 disclosed a method of treatment of acne vulgaris which comprises systemic administration to a patient suffering from acne vulgaris divided doses about 1 to 5 times a day of a combination of pharmaceutical agents consisting essentially of approximately 2 to 10 grams pantothenic acid, approximately 0.3 to 3 grams nicotinic acid, and approximately 5 to 50 milligrams biotin.

The available drugs have been discovered by the methods of classical pharmacology, which while sometimes highly successful are always complex, laborious, time-consuming and costly. For an overview of the entire process from the proposal of an idea by a researcher to the initiation of clinical trials of a remedy, reference can be had to "Natural History of a Typical Drug" a chapter by Dr. E. L. Harris in "The Principles and Practice of Clinical Trials" (Harris and Fitzgerald, editors, E. & S. Livingstone, Edinburgh and London, 1970). Harris writes "The first stage is that of the idea. Whatever the source of the idea, it is considered by a research panel consisting of medical, chemical, pharmacological, pharmaceutical and commercial interests. If the panel feel that the idea has merit, then the research chemist sets about synthesising the compound or a number of related compounds. This can be a very long and arduous task; it has been estimated that synthesis and initial biological screening of a single compound can take up to 400 man hours to achieve . . .

When sufficient quantities have been made the pure drugs are handed over to the pharmacologist who carries out a programme of empirical screening tests, designed to cover as wide a range of pharmacological actions as economically as possible so as to expose any effects which might be of therapeutic use. If an anction is detected more detailed experiments to elucidate this are carried out.

Many compounds are rejected at this stage either because of lack of activity or gross toxicity. Those that do survive are again considered by the research panel who decide whether the agent has sufficient promise to go forward to assess its safety in animals.

There are three phases in toxicity testing. The first is the acute toxicity study which deals with the quantitative assessment of the short term effects of a drug. The response is noted after a single oral or parenteral dose, or several doses given within 24 hours. These tests are carried out in a variety of species.

The next is sub-acute toxicity, and in general covers repeated dosage in at least two species, such as mice and rats, for periods up to 90 days. An additional non-rodent species, eg. dog, is often included.

Chronic studies are for the duration of life in the animal— rats and mice are suitable. Occasionally long term studies are employed in other animals such as dogs and monkeys for periods up to two years . . .

When the exacting toxicological studies are completed and the research panel is satisfied with all the data that has been generated, the drug is administered to healthy volunteers. . ."

Against this background, there clearly exists a need for improved remedies and preventive methods for facial pimples or acne, and improved methods for their discovery.

SUMMARY OF THE INVENTION

In accordance with this invention, I have found that I can reproducibly cause a susceptible human subject to experience a measurable and reproducible appearance of facial pimples within a short period of time upon the oral administration of a sufficient quantity of any of a class of substances which I propose to call trigger substances. These trigger substances are foods in widespread consumer use and are without effect on the great majority of the human population. In a susceptible subject, however, the effect is both reproducible and sufficiently long lasting to serve as research tool for the evaluation of agents effective in preventing the appearance of face pimples as in acne. Accordingly, the method of determining the effectiveness of an agent for prevention of facial pimples or acne comprises the steps of a) administering to a susceptible subject a quantity of a trigger substance reproducibly effective in producing within a period of four hours the appearance of at least two pimples on the face of the subject lasting for at least eight hours in the absence of treatment, b) administering to said subject having received said quantity of trigger substance a predetermined quantity of the agent whose effectiveness is to be determined, c) measuring the number of pimples on the face of the subjectg upon administering said agent, and d) comparing the number of pimples with and without the administration of said agent.

Also in accordance with this invention, I have found that effective quantities of certain nutrient substances can reproducibly prevent appearance of pimples on the face of a susceptible subject following the administration of a trigger substance. Being nutrient substances that are ingested and metabolized by humans daily, such substances are inherently safe. Accordingly, the method of preventing the appearance of pimples in a person in need of such relief, comprises the administration to such person of a quantity of an agent determined to be effective in preventing the appearance of pimples on the face of a susceptible subject following the administration of a trigger substance. Such administration of an agent can take place before the administration of a trigger substance or at the same time as a trigger substance is administered, so that the appearance of pimples that would be produced without the agent is thereby prevented.

Also in accordance with this invention, I have found that an agent found effective in accordance with this invention in preventing the appearance of face pimples can be combined with a pharmaceutically acceptable carrier to provide an effective palatable acne preventing remedy composition. Moreover, I have found that a combination of two or more selected agents found effective in accordance with this invention in preventing the appearance of face pimples can be combined with a pharmaceutically acceptable carrier to provide a pleasant tasting as well as effective and palatable acne preventing remedy composition.

DESCRIPTION OF PREFERRED EMBODIMENTS

Trigger Substances

A trigger substance according to this invention is defined as any substance that, when administered to a susceptible human subject, reproducibly gives rise to the appearance of at least two pimples on the face of such subject in a time period of four hours or less. Preferred trigger substances are those known to be safe to administer to a human subject, particularly substances known to be in consumer use or authoritatively regulated for such use under observance of appropriate limitations. Included among such trigger substances are certain common foods and substances commonly added to foods to improve their taste, texture, mouth feel and palatability in general such as fats and oils, especially polyunsaturated oils and oils and fats used in deep frying and other methods of processing food at elevated temperatures, such as 120° C. and even higher. An immediate effect of such fats and oils in triggering the appearance of face pimples within eight hours or less has not previously been reported.

Trigger substances can also include whole products in which it may or may not be possible to identify a particular ingredient as responsible for the trigger effect. Such products include french fries and other high fat forms of potatoes as served in many large fast food chain establishments or sold frozen for home use and certain meats and meat products, especially pork processed by such techniques as roasting, baking, frying, smoking, curing or sausage making. Whether the trigger substance in such fats and oils, potato preparations, or meats and meat products be the product itself or minor constituents possibly contained therein, or a combination of both, or neither of these, is less important than that a reproducible trigger effect has been observed.

The quantitity of trigger substance to be administered for appearance of face pimples to be reproducible is readily determined empirically. For example, a reproducible appearance of two face pimples within eight hours or less has been noted by a susceptible individual upon consumption of two "large" portions of french-fried potatoes as served in a fast food establishment.

Agents Effective in Preventing Appearance of Face Pimples

In accordance with this invention, any desired agent can be tested for its effectiveness in preventing the appearance of face pimples otherwise produced in a susceptible individual by administration of a trigger substance. The only limitation is the practical requirement of not doing harm to such individual. For that reason, I have sought effective agents principally among substances known to be safe to administer to a human subject, particularly substances known to be nutrients ingested and metabolized by human beings on a daily or at least frequent basis. I have tested many nutrient substances and found effective among these a restricted group of water soluble aminocarboxylic acid compounds at dose levels in the range from 200 to 20000 milligrams. I use the term water soluble to refer to a solubility of at least three grams in 100 ml of water at 25° C.

A preferred group of water soluble aminocarboxylic acid compounds effective according to this invention in preventing appearance of face pimples can be represented by formula (I):

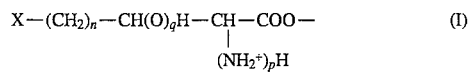

in which X is selected from the group consisting of —SH, —CONH$_2$,

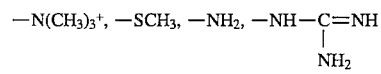

and

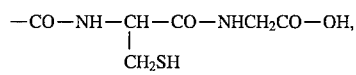

n is zero, one, two, or three, and p and q are each zero or one, provided that p and q are not both zero and p is zero and q is one only when X is –N(CH$_3$)$_3$+.

Table 1 which follows includes particularly preferred water soluble aminocarboxylic acid compounds represented by formula (I) which I have found effective in preventing appearance of face pimples when administered before or together with a trigger substance.

TABLE 1

| # | Name | X | n | p | q |
|---|------|---|---|---|---|
| 1 | 2-amino-3-mercaptopropanoic acid | —SH | 0 | 1 | 0 |
| 2 | 2-amino-4-carbamoylbutanoic acid | —CONH$_2$ | 1 | 1 | 0 |
| 3 | 2-amino-4-methylthiobutanoic acid | —SCH$_3$ | 1 | 1 | 0 |
| 4 | 2,5-diaminopentanoic acid | —NH$_2$ | 2 | 1 | 0 |
| 5 | 2,6-diaminohexanoic acid | —NH$_2$ | 3 | 1 | 0 |
| 6 | 2-amino-5-guanidopentanoic acid | —NH—C(=NH)—NH$_2$ | 2 | 1 | 0 |
| 7 | 2-(4-amino-5-carboxypentanoamido)-3-mercapto-N-carboxymethylpropanoamide | —CO—NH—CH(CH$_2$SH)—CO—NHCH$_2$CO—OH | 1 | 1 | 0 |
| 8 | 3-hydroxy-4-trimethylammoniobutanoate | —N(CH$_3$)$_3$+ | 1 | 0 | 1 |

Formula (I) and all the effective compounds listed in Table 1 contain an assymetric carbon atom and hence exist in non-superimposable optically active forms (so-called D and L forms) and in racemic mixtures or DL forms. Both D and L forms of the effective compounds and racemic mixtures thereof are contemplated in accordance with this invention.

There is nothing about the structures of the effective compounds of this invention or their known nutrient properties that would have enabled one to predict their effectiveness in preventing appearance of face pimples in accordance with this invention. This unpredictability is further underscored by the finding that a number of aminocarboxylic acid compounds structurally similar to those effective according to this invention but not structured according to formula (I) are ineffective. In Table 2 following, there are listed a number of aminocarboxylic acid compounds found ineffective in preventing appearance of face pimples when administered together with a trigger substance. Some of these compounds can be represented by formula (II)

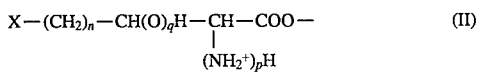

$$X—(CH_2)_n—CH(O)_qH—CH(NH_2^+)_pH—COO— \quad (II)$$

in which the assignments of X and/or n differ from those in formula (I)

TABLE 2

| # | Name | X | n | p | q |
|---|------|---|---|---|---|
| A | 2-aminopropanoic acid | hydrogen | 0 | 1 | 0 |
| B | 2-amino-3-phenylpropanoic acid | phenyl | 0 | 1 | 0 |
| C | 2-amino-3-imidazolylpropanoic acid | imidazolyl | 0 | 1 | 0 |
| D | 2-aminoacetic acid | not applicable | not applicable | | |
| E | 2-aminopentanedioic acid | —COOH | 2 | 1 | 0 |

While these substances are ineffective in preventing appearance of face pimples, they do not act as trigger substances and thus can be present in modest amounts as companion substances to effective agents according to this invention. In this way such substances can contribute to the useful properties of the effective agents by enhancing their speed of action, palatability and/or taste characteristics. When present as companion substances to effective agents their concentration will typically range from 1 to 10 weight percent of the effective agent.

Palatable Oral Dosage Forms

Also in accordance with this invention, a pharmaceutically acceptable carrier can be combined with effective amounts of an effective agent according to this invention to provide a palatable oral dosage form for administering to a person in need of preventing appearance of face pimples. Accordingly, palatable oral dosage forms according to this invention comprise at least one pharmaceutically acceptable carrier and an effective amount of an effective agent according to this invention. Preferably the effective agent is an aminocarboxylic acid nutrient compound having formula (I). Particularly preferred effective agents are those listed in Table 1.

One preferred palatable oral dosage form according to this invention is a tablet. A particularly preferred tablet according to this invention comprises a high percentage of at least one aminocarboxylic acid nutrient compound having formula (I) and minor amounts of carrier material acting as binder for the tablet. Suitable binder materials include naturally occurring carbohydrates such as cellulose, starch, galactomannan, fructose, lactose, and sucrose; finely divided ingestible mineral substances such as calcium and magnesium carbonates, calcium and magnesium silicates, calcium and magnesium phosphates, alumina hydrates and hydrotalcite; waxy materials such as beeswax, stearin, stearates of calcium, magnesium, and aluminum, microcrystalline wax and paraffin, and mixtures thereof.

Another preferred palatable oral dosage form according to this invention is a capsule. Capsules have the advantage of delivering the effective agent directly to the alimentary canal without being tasted in the mouth. Suitable capsules are commercially available and are typically made of gelatin, but any sufficiently pure water soluble polymer can be used. Preferably the capsule is filled with the pure aminocarboxylic acid nutrient compound having formula (I); alternatively, suspensions of aminocarboxylic acid nutrient compound having formula (I) in a liquid carbohydrate such as corn syrup or honey, or in a lipid such as lecithin or canola oil can be encapsulated.

A further palatable oral dosage form according to this invention comprises an effective amount of an effective agent according to this invention in a liquid carrier such as a prepared soup or a fruit flavored drink.

Preferably the effective agent is an aminocarboxylic acid nutrient compound having formula (I). Particularly preferred effective agents are those listed in Table 1.

Suitable prepared soups include all flavors of canned and dehydrated soups, preferably in containers sized so as to deliver a single serving of soup containing an appropriate dose of the effective agent.

Suitable fruit flavored drinks include natural fruit juices such as pineapple juice, apple juice, grape juice, orange juice, grapefruit juice, cranberry juice, and mixtures thereof; reconstituted juices prepared from water and fruit juice concentrates, and fruit juice drinks containing water and at least 10% of natural fruit juice.

In oral dosage forms according to this invention, the proportions of carrier to effective agent can vary over a broad range in accordance with the kind of carrier selected and the strength desired. Thus the proportion of carrier can be as little as 0.1% by weight, as in a tablet, and as high as 85% or even more, as in a fruit flavored drink.

Tablets in accordance with this invention can be prepared, for example, from 750 milligrams of each of compounds #1, 3, 5, 7, or 8 of Table 1 and 5 milligrams each of stearin, magnesium stearate, and magnesium silicate. Capsules in accordance with this invention can be prepared, for example, by filling elliptical capsules of 1.5 ml capacity with 500 milligrams of each of compounds #1, 2, 3, 4, 5, 6, 7, or 8 of Table 1.

Fruit flavored drinks in accordance with this invention can be prepared, for example, from 3750 milligrams of each of compounds #1, 2, 3, 4, 5, 6, 7, or 8 of Table 1 and 75 milliliters of commercially available apple-cranberry drink.

Pleasant Tasting Oral Dosage Forms

Also in accordance with this invention, a pharmaceutically acceptable carrier can be combined with effective amounts of an effective agent according to this invention and a flavorant to provide a pleasant tasting oral dosage form for administering to a person in need of preventing appearance of face pimples. Accordingly, pleasant tasting oral dosage forms according to this invention comprise at least one pharmaceutically acceptable carrier, an effective amount of an effective agent according to this invention, and a flavorant. Preferably the effective agent is an aminocarboxylic acid nutrient compound having formula (I). Particularly preferred effective agents are those listed in Table 1.

Preferred flavorants that can be used in a pleasant tasting oral dosage form according to this invention include herbs such as basil, cilantro, dill, oregano, tarragon, and thyme; spices such as cinnamon, clove, ginger, mace, and nutmeg, and essential oils such as oil of lemon, oil of orange, oil of peppermint, and oil of sassafras.

In a particularly preferred pleasant tasting oral dosage form according to this invention, there are present in amounts selected to complement the taste characteristics of each at least one first nutrient compound having the formula

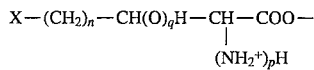

in which X is selected from the group consisting of
—NH$_2$, and

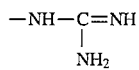

, n is two or three, p is one and q is zero, and at least one second nutrient compound having the formula

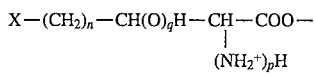

in which X is selected from the group consisting of —SH, —CONH$_2$, —N(CH$_3$)$_3$+, —SCH$_3$, and

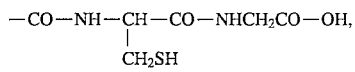

n is zero or one, and p and q are each zero or one, provided that p and q are not both zero and p is zero and q is one only when X is —N(CH$_3$)$_3$+.

In such compositions, the taste characteristics of the first nutrient compound and the second nutrient compound interact in such a way as to produce an overall pleasant tasting composition.

Pleasant tasting tablets in accordance with this invention can be prepared, for example, from 750 milligrams of each of compounds #1, 3, 5, 7, or 8 of Table 1, 5 milligrams each of stearin, magnesium stearate, and magnesium silicate, and 10 milligrams of finely powdered cinnamon.

A pleasant tasting fruit flavored drink in accordance with this invention can be prepared, for example, by blending 4500 milligrams of each of compounds #1, 3, 5, 7, or 8 of Table 1, 110 milliliters of commercially available chilled grapefruit juice, and 5 drops oil of orange.

Pleasant tasting tablets containing a first nutrient compound and a second nutrient compound in accordance with this invention can be prepared, for example, from 500 milligrams of each of compounds #1, 2, 3, 5, 7, or 8 of Table 1, 250 milligrams of each of compounds #4 or 6 of Table 1, and 5 milligrams each of stearin, magnesium stearate, and magnesium silicate.

The following Examples are provided to illustrate the invention without intending to limit its scope, which is defined by the appended claims.

EXAMPLE 1

So-called "large" portion quantities of french-fried potatoes as served in large fast food chains were fed on alternate days on an empty stomach and in the absence of other foods to a male human subject known to be susceptible to acne believed to be associated with the consumption of high fat content foods. The following observations were recorded

| Trial | Number of "large" portions | Number of pimples on face at time shown: | | | |
|---|---|---|---|---|---|
| | | before eating | 2 hour after | 4 hours after | 8 hours after |
| a | 1 | 1 | 1 | 2 | 2 |
| b | 2 | 1 | 1 | 3 | 4 |
| c | 3 | 1 | 1 | 4 | 6 |

The results show that two or more "large" portion quantities of french-fried potatoes as given in these trials are clearly sufficient to trigger a marked dose-related increase in facial pimples in this individual.

EXAMPLE 2

Quantities of pan fried pork sausage were fed on alternate days on an empty stomach and in the absence of other foods to a female human subject whose face was free of pimples at the start. The following observations were recorded.

| Trial | Quantity | No. of pimples four hours after eating |
|-------|----------|----------------------------------------|
| a     | 50 gram  | none                                   |
| b     | 100 gram | 1                                      |
| c     | 150 gram | 2                                      |
| d     | 200 gram | 3                                      |

The results show that the quantities of pork sausage given in trials b, c, and d are clearly sufficient to trigger a marked incidence of pimples in this individual.

EXAMPLES 3–4 AND COMPARISON TRIALS 1 AND 2

In each of the following trials, a quantity of two "large" portions of french fried potatoes as served in large fast food chains was fed on alternate days on an empty stomach and in the absence of other foods to the same male human subject as in Example 1. At the same time, there was administered a dose of a substance as noted below. The subject's face was observed at two hour intervals.

| Example no. | Substance | Dose | No. pimples at time after administration, hours | | | |
|-------------|-----------|------|---|---|---|---|
|             |           |      | 2 | 4 | 6 | 8 |
| 3           | Blend of substances from Table 1 | 2000 mg | 1 | 1 | 2 | 2 |
| 4           | Blend of substances from Table 1 | 4000 mg | 1 | 1 | 1 | 1 |
| Comparison 1 | none     |      | 1 | 3 | 3 | 4 |
| Comparison 2 | blend of substances from table 2 | 4000 | 1 | 3 | 3 | 4 |

The results show the blend of substances shown in Examples 3 and 4 was an effective agent according to this invention in preventing the incidence of pimples triggered by consumption of fatty food in accordance with a method of this invention. The results also show that compounds of Table 2 with structural similarity to those effective according to this invention but differing in the assignments of X and/or n in the formula were ineffective.

I claim:

1. The method of treating facial pimples in a person in need of such prevention, comprising the oral administration to such person of an effective amount of at least one nutrient compound having the formula $$X-(CH_2)_n-CH(O)_qH-CH(NH_2^+)_pH-COO-$$

in which X is selected from the group consisting of $-CONH_2$,

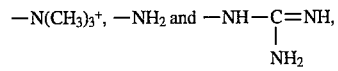

n is zero, one, two, or three and p and q are each zero or one, provided that p and q are not both zero and p is zero and q is one only when X is $-N(CH_3)_3^+$.

2. The method of claim 1 in which X is $-CONH_2$ and n is one.

3. The method of claim 1 in which X is $-NH_2$ and n is two, p is one and q is zero.

4. The method of claim 1 in which X is $-NH_2$ and n is three.

5. The method of claim 1 in which X is

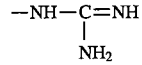

and n is two.

6. The method of claim 1 in which X is $-N(CH_3)_{3+}$, n is zero, p is zero, and q is one.

* * * * *